United States Patent
Naor et al.

(10) Patent No.: US 7,742,171 B2
(45) Date of Patent: Jun. 22, 2010

(54) REFLECTIVITY/EMISSIVITY MEASUREMENT PROBE INSENSITIVE TO VARIATIONS IN PROBE-TO-TARGET DISTANCE

(75) Inventors: Yoram Naor, Givat Elah (IL); Benjamin J Brosilow, Ramat Yishay (IL)

(73) Assignee: CI Systems Ltd., Migdal Haemek (IL)

( * ) Notice: Subject to any disclaimer, the term of this patent is extended or adjusted under 35 U.S.C. 154(b) by 345 days.

(21) Appl. No.: 11/834,030

(22) Filed: Aug. 6, 2007

(65) Prior Publication Data

US 2009/0040506 A1 Feb. 12, 2009

(51) Int. Cl.
G01N 21/55 (2006.01)
(52) U.S. Cl. .................................... 356/448
(58) Field of Classification Search ............... 356/447, 356/448
See application file for complete search history.

(56) References Cited

U.S. PATENT DOCUMENTS

| | | | |
|---|---|---|---|
| 3,433,052 A | 3/1969 | Maley | |
| 4,708,493 A | 11/1987 | Stein | |
| 4,710,627 A * | 12/1987 | Baltes et al. | 250/339.11 |
| 4,919,542 A | 4/1990 | Nulman et al. | |
| 4,950,905 A * | 8/1990 | Butler et al. | 250/358.1 |
| 6,299,346 B1 | 10/2001 | Ish-Shalom et al. | |
| 7,218,386 B2 * | 5/2007 | Alcock et al. | 356/71 |
| 7,262,854 B2 * | 8/2007 | Imura | 356/402 |
| 2005/0286053 A1* | 12/2005 | Imura | 356/402 |
| 2006/0268283 A1* | 11/2006 | Zaldo Luezas et al. | 356/600 |

* cited by examiner

Primary Examiner—Roy Punnoose
(74) Attorney, Agent, or Firm—Mark M. Friedman

(57) ABSTRACT

Apparatuses and methods for accurately measuring the reflectivity of a target surface, under conditions where the distance between a measuring probe and the target surface is not fixed. At least two measurements of the target reflectivity are taken under different conditions, and then these two or more measurements are combined in order to calculate the target reflectivity in a way which is independent of the probe-to-target distance. In particular, the different conditions are such that each measurement samples radiation reflected from the target surface at a different distribution of angles. The apparatus can also be used to accurately measure the distance between the probe measurement head and a target surface.

25 Claims, 10 Drawing Sheets

FIG 1B SIDE VIEW OF 1A
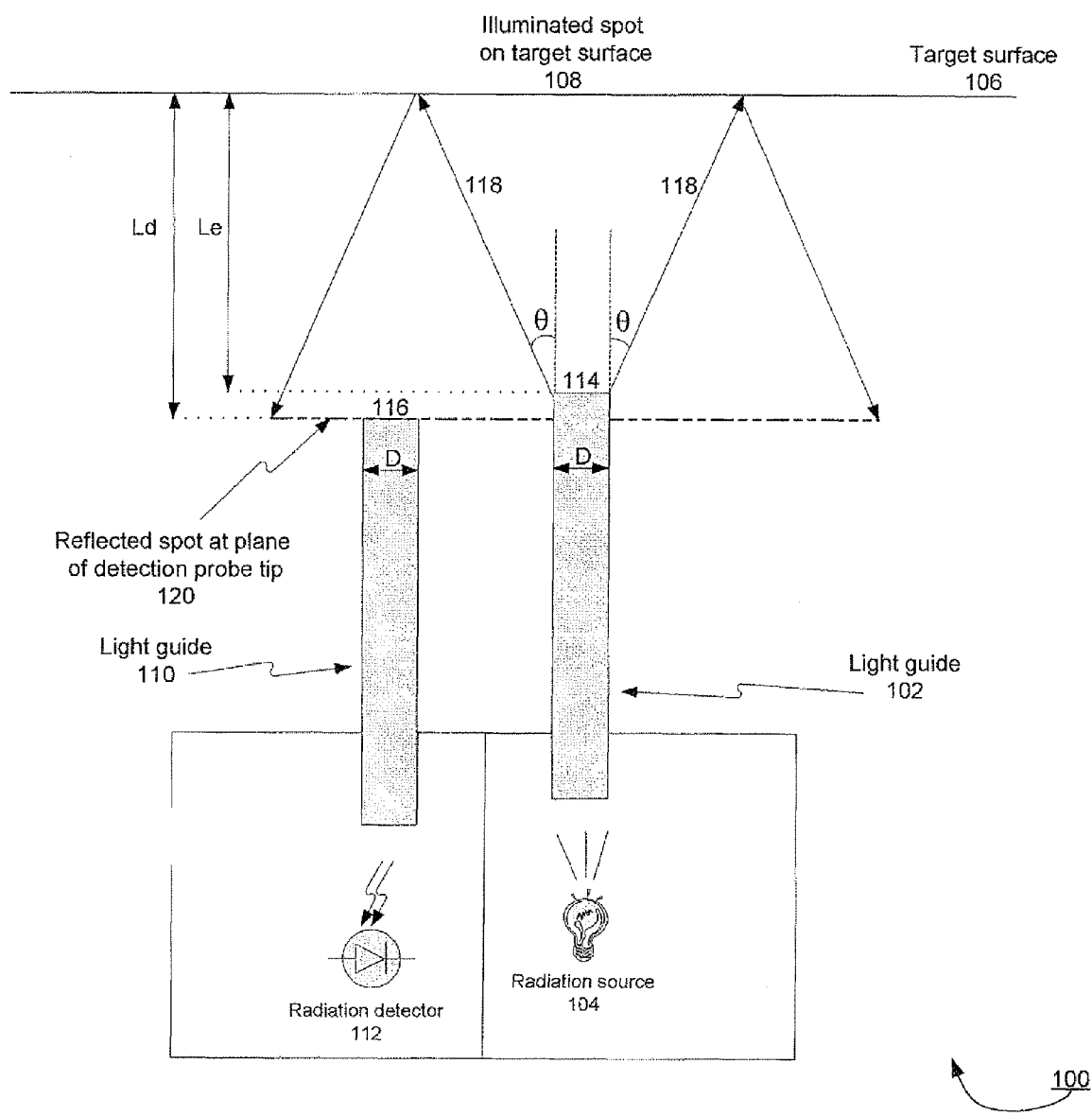

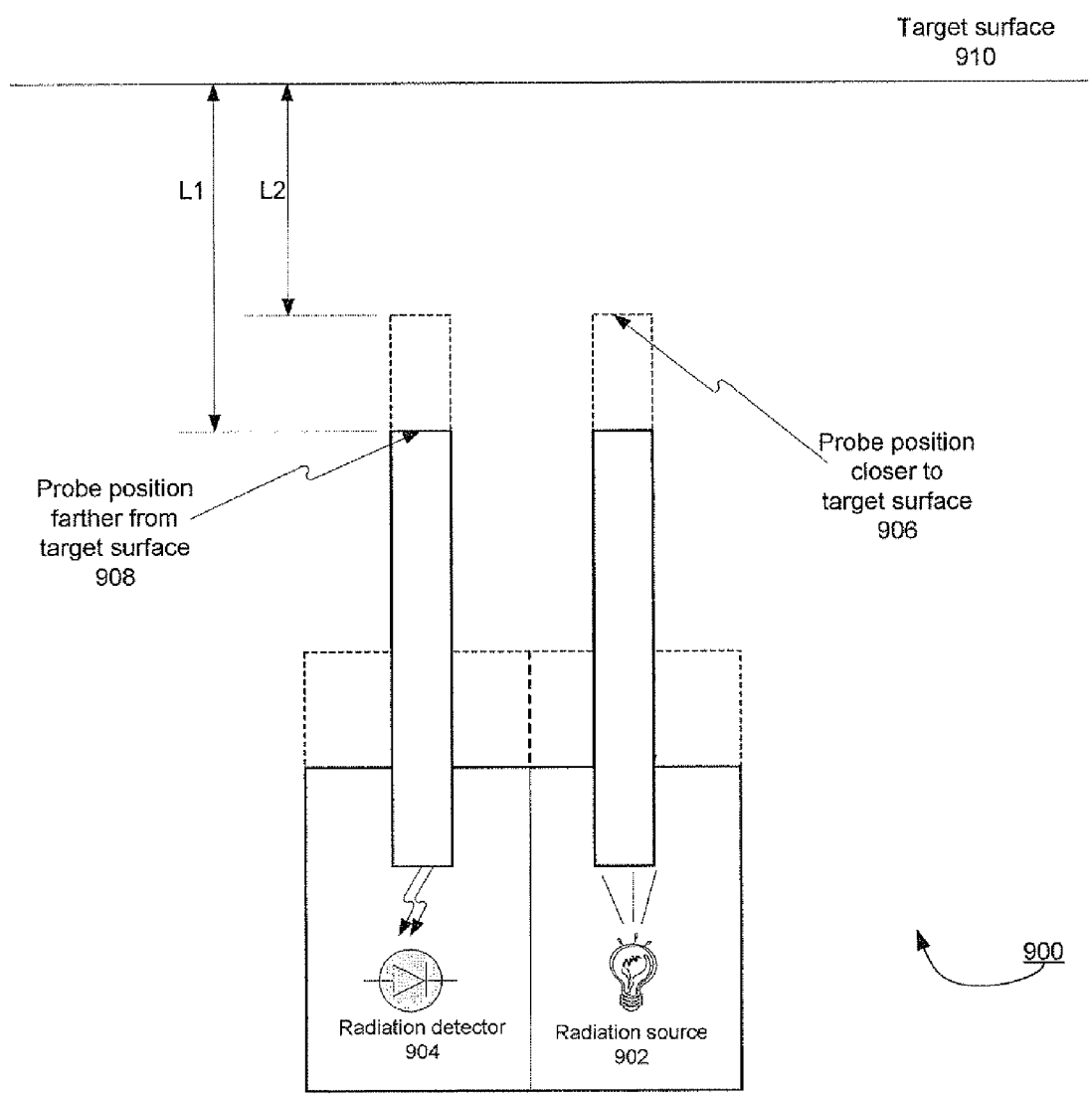

US 7,742,171 B2

REFLECTIVITY/EMISSIVITY MEASUREMENT PROBE INSENSITIVE TO VARIATIONS IN PROBE-TO-TARGET DISTANCE

FIELD OF THE INVENTION

The present invention relates in general to reflectivity measurement systems, and in particular to systems in which the reflectivity measurement is ultimately used alone or in combination with other measurements to determine a target object's emissivity and/or temperature.

BACKGROUND OF THE INVENTION

The reflectivity of a target surface can be measured by irradiating the surface and measuring the fraction of the incident radiant energy that is reflected. Apparatuses and methods to perform such measurements are known, see for example the Delta and NTM500 radiation thermometers manufactured by C I Systems (P.O. Box 147, Migdal Ha'emek 10051 Israel) and the Optitherm III radiation thermometer manufactured by the Pyrometer Instrument Company (92 North Main Street, Bldg 18-D, Windsor, N.J. 08561, USA), among others. Apparatuses to perform such measurements are also described in e.g. U.S. Pat. Nos. 3,433,052, 4,708,493, 4,919,542, and 6,299,346, and in the patents referenced therein.

A schematic drawing of an exemplary prior art apparatus 100 for performing such a measurement is shown in FIGS. 1A and 1A. Apparatus 100 includes a light guide 102 that directs radiation from a radiation (e.g. light) source 104 onto a target surface 106 to form an illuminated spot 108. A fraction of the radiation reflected by the target surface is incident on a second light-guide 110, which directs this radiation to a detector 112. Frequently, there may be an optical filter (not shown) placed somewhere in the optical path between radiation source 104 and detector 112 so that the apparatus will be sensitive only to reflected radiation within a given radiation wavelength range.

For the apparatus sketched in FIGS. 1A and 1B, with a constant radiation-source intensity and constant geometry, the target surface reflectivity $\rho$ can be determined from the relationship:

$$V = V_0 + \rho V_1 \quad (1)$$

where V is the radiant intensity incident on detector 112, $V_0$ is an offset term arising due to non-idealities in the apparatus, such as e.g. internal reflections within the apparatus, offsets in the detector, etc. and $V_1$ is a proportionality constant that depends on the apparatus design and its positioning relative to the target surface. Examples of parameters effecting the value of the constant $V_1$ include; the apparatus' radiation source intensity, the apparatus' radiation transmission efficiency, and the distances $L_d$ and $L_e$ between the target surface and two probe tips 114 and 116 of light-guides 102 and 110 respectively.

Typically, equation (1) is used to determine target reflectivity after a calibration procedure that consists of two steps. First, $V_0$ is determined by measuring the signal V when the probe views a target of zero reflectivity. This measurement is typically performed by directing the probe at a large open space, from which no reflection is returned to the probe. Next, a target calibration surface with a known reflectivity $\rho_{calibration}$ is placed in front of the probe, at the same distance and orientation with respect to the probe at which subsequent measurements are to be taken. A signal $V = V_{calibration}$ is generated while measuring this target. This calibration step is used to calculate $V_1$ of equation (1) as $V_1 = (V_{calibration} - V_0)/\rho_{calibration}$. Once $V_1$ is known, equation (1) can be rearranged into a form which can be used to determine the reflectivity of all subsequently measured surfaces:

$$\rho = \rho_{calibration} \frac{V - V_0}{V_{calibration} - V_0} \quad (2)$$

Note that typically the incident radiation source is modulated, in which case the measured signal V is the amplitude of the fluctuation in reflected intensity, rather than an absolute intensity measurement. This allows the reflectivity measurement to be insensitive to the presence of reflected radiation from other interfering radiation sources and from the target's self-emission.

The existing reflectivity measurement apparatuses and methods suffer from the disadvantage that the reflected signal V is a strong function of the probe-to-target distance. Hence, significant errors in the measured reflectivity value can occur if the target surface moves relative to the position at which the calibration target was placed. The sensitivity of the measurement to variations in the probe-to-target distance is illustrated by a simple example, explained with reference to FIG. 1B. Consider a probe 102 of the general type shown in FIG. 1B, which emits from its probe-tip 114 a beam of radiation with uniform intensity within a cone-section 118 of apex angle 2θ. Consider the case where the emitted beam is incident on a specularly reflecting target surface 106. In this exemplary case, equation 1 can be written in the following form:

$$V = V_0 + \rho \eta \frac{\pi (D/2)^2}{\pi (D/2 + (L_e + L_d)\tan\vartheta)^2} \quad (3)$$

Here D is the diameter of both the radiation source and detector light-guides, $L_e$ and $L_d$ are the distances between each of these respective light-guides and the target surface (see FIG. 1A), and η is a proportionality constant that accounts for the intensity emitted by the apparatus' radiation source, the transmission efficiency of the apparatus optics, etc. The ratio in the second term in equation (3) is the ratio of the cross-sectional area of collecting light-guide 110 divided by a cross-sectional area 120 of the reflected beam as it intersects this light-guide. Since the beam has uniform intensity within the cone-section in this example, this ratio represents the fraction of the total reflected power which is collected by the probe. Solving equation (3) for the reflectivity ρ, gives:

$$\rho = \frac{(V - V_0)}{\eta}\left(1 + 4\frac{L}{D}\tan\vartheta\right)^2 \quad (4)$$

where we define an probe-to-target distance L to be $L = (L_e + L_d)/2$. That is, L is the average distance between the two probe tips and the target surface. If such a probe is now used to measure a calibration target with reflectivity $\rho_{calibration}$, at a calibration probe-to-target distance $L=L_{calibration}$, then the measured signal $V_{calibration}$ will satisfy relationship (4):

$$\rho_{calibration} = \frac{(V_{calibration} - V_0)}{\eta}\left(1 + 4\frac{L_{calibration}}{D}\tan\vartheta\right)^2 \quad (5)$$

Equation (5) can be substituted into (4) to eliminate $\eta$, and obtain:

$$\rho = \rho_{calibration}\frac{(V - V_0)}{(V_{calibration} - V_0)}\frac{\left(1 + 4\frac{L}{D}\tan\vartheta\right)^2}{\left(1 + 4\frac{L_{calibration}}{D}\tan\vartheta\right)^2} \quad (6)$$

When $L=L_{calibration}$, equation (6) is reduced to equation (2) and an accurate reflectivity measurement is achieved using equation (2) and the procedures described previously. However, when $L \neq L_{calibration}$, an error is introduced into the measurement. The fractional error in the measured reflectivity is given by:

$$\frac{\rho_{measured}}{\rho_{actual}} = \frac{\left(1 + 4\frac{L_{calibration}}{D}\tan\vartheta\right)^2}{\left(1 + 4\frac{L}{D}\tan\vartheta\right)^2} \quad (7)$$

This fractional error is plotted in FIG. 2 as a function of L/D for $\theta=30°$ and $L_{calibration}=D$. This figure shows that when the probe moves away from its nominal position by half a probe diameter (D/2) the measured reflectivity is 0.56 times its actual value, while if the probe moves half a probe diameter closer to the target compared to the nominal position, then the measured reflectivity is 2.36 times its actual value.

Note that while equations (3) to (7) are specific to the model system described in this section, the $\sim 1/L^2$ dependence of the fractional reflectivity error in equation (7) is a general feature of such measuring systems, which typically show roughly inverse quadratic dependence on probe-to-target distance, since the divergence of the radiation beam emitted by the apparatus is a two-dimensional phenomenon.

There is therefore a need for and it would be advantageous to have a reflectivity measurement probe that is insensitive to variations in the distance between the probe and the target surface.

SUMMARY OF THE INVENTION

The present invention discloses apparatuses and methods for accurately measuring the reflectivity of a target surface (also referred to as "reflectivity meters"), under conditions where the distance between the measuring probe and the target surface is not fixed.

According to the present invention there is provided an apparatus for determining the reflectance of a target surface including a radiation source for projecting radiation onto the target surface and a radiation detector positioned to detect radiation reflected off the target surface and to produce at least two signals V1 and V2 such that each signal is indicative of a radiation intensity reflected at a respective angular distribution that is different for each signal, whereby signals V1 and V2 are used to calculate the reflectivity of the target surface.

According to the present invention there is provided an apparatus for determining the reflectance of a target surface including a radiation source for projecting radiation onto the target surface, a radiation detector positioned to detect radiation reflected off the target surface and to produce at least two signals V1 and V2 such that each signal is indicative of a radiation intensity reflected at a respective angular distribution that is different for each signal, wherein signals V1 and V2 differ from each other in that each respective angular distribution is determined by a respective different probe tip.

According to the present invention there is provided a method for determining the reflectance of a target surface including the steps of detecting radiation reflected from the target surface in at least two different angular distributions, each angular distribution producing a respective different reflected radiation intensity value and calculating the target reflectivity from the at least two different reflected radiation intensity values.

In some embodiments, the step of detecting is performed sequentially by a single radiation detector.

In some embodiments, the step of detecting is performed simultaneously by using a dedicated radiation detector for each angular distribution.

In some embodiments, the different angular distributions are induced by illuminating the target surface with different illumination spot sizes.

In some embodiments, the different angular distributions are induced by passing the reflected radiation through different size apertures positioned between the target surface and respective different radiation detectors.

In some embodiments, the different angular distributions are induced by illuminating the surface with radiation originating from at least two probe tips positioned at different distances from the target surface.

In some embodiments, the different angular distributions are induced by illuminating the surface with radiation originating from at least two probe tips having different diameters.

In some embodiments, the step of calculating includes detecting radiation reflected from a target surface of near zero reflectivity in at least two different angular distributions and producing at least two respective signals V01 and V02 indicative of the radiation intensity at respective angular distributions 1 and 2, generating a calibration function $f$ by performing the step of detecting on a target of known reflectivity $\rho_{calibration}$ and using signals V01 and V02 and calibration function $f$ to calculate the target reflectivity.

In some embodiments, the different angular distributions are achieved through reflected radiation emanating from multiple radiation sources, wherein the intensity of each radiation source is modulated with a different frequency and/or phase.

BRIEF DESCRIPTION OF THE DRAWINGS

The invention is herein described, by way of example only, with reference to the accompanying drawings, wherein.

FIG. 1B shows a side view of the apparatus of FIG. 1A.

FIG. 9 shows a schematic drawing of another reflectivity meter of the present invention, using a probe consisting of one detector and one radiation source, where the probe tip is moved between two positions relative to the target surface.

DETAILED DESCRIPTION OF THE INVENTION

In order to overcome the dependence of the described reflectivity measurement on variations in the probe-to-target distance, the present invention suggests apparatuses and methods in which at least two measurements of the target reflectivity are taken under different conditions. These at least two measurements are then combined in order to calculate the target reflectivity in a way that is independent of the probe-to-target distance. In particular, the "different conditions" required for each measurement are such that each measurement samples radiation reflected from the target surface at a different distribution of angles.

Figure 1A:
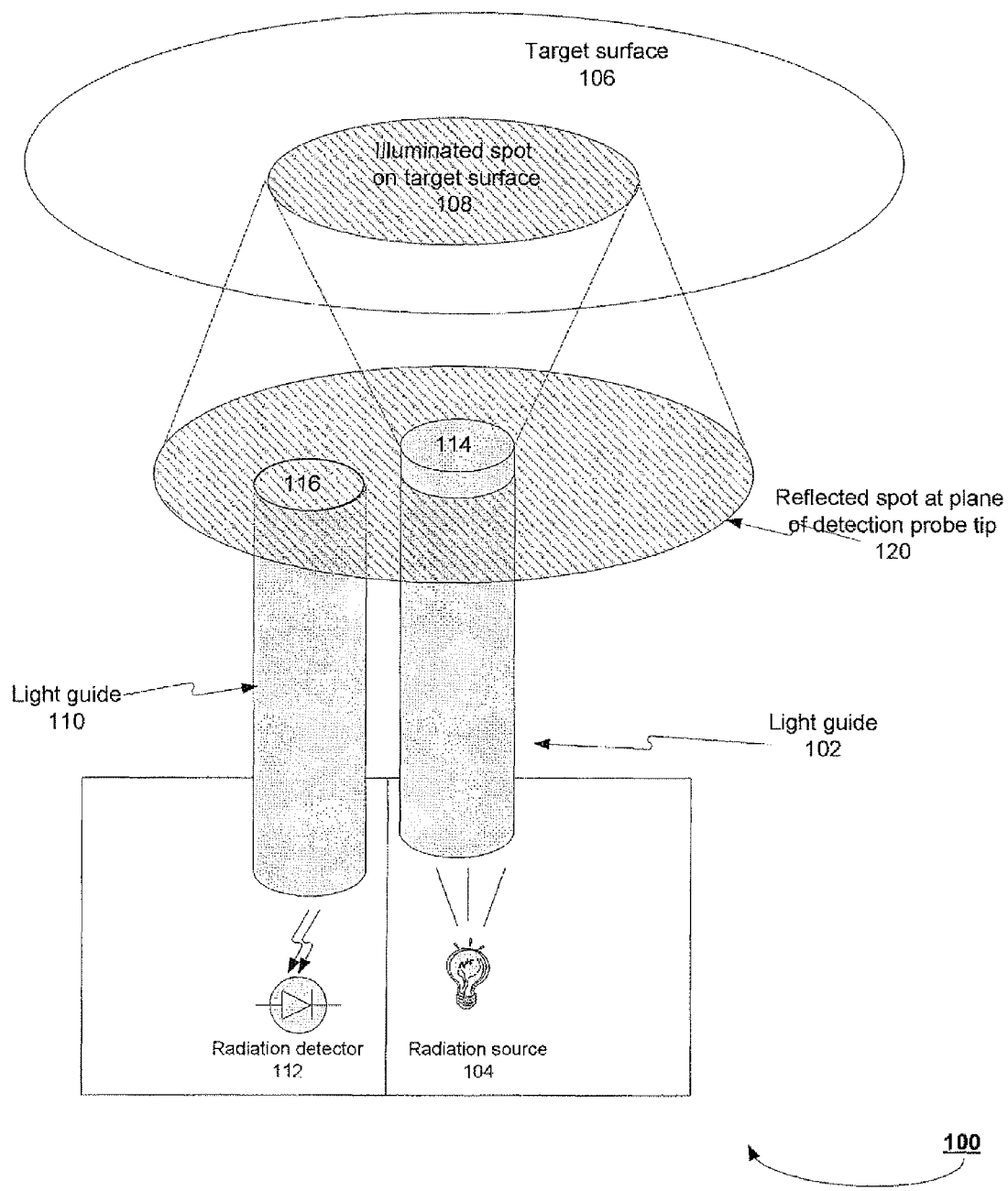
FIG. 1A shows a prior art apparatus for measuring reflectivity.
Figure 2:
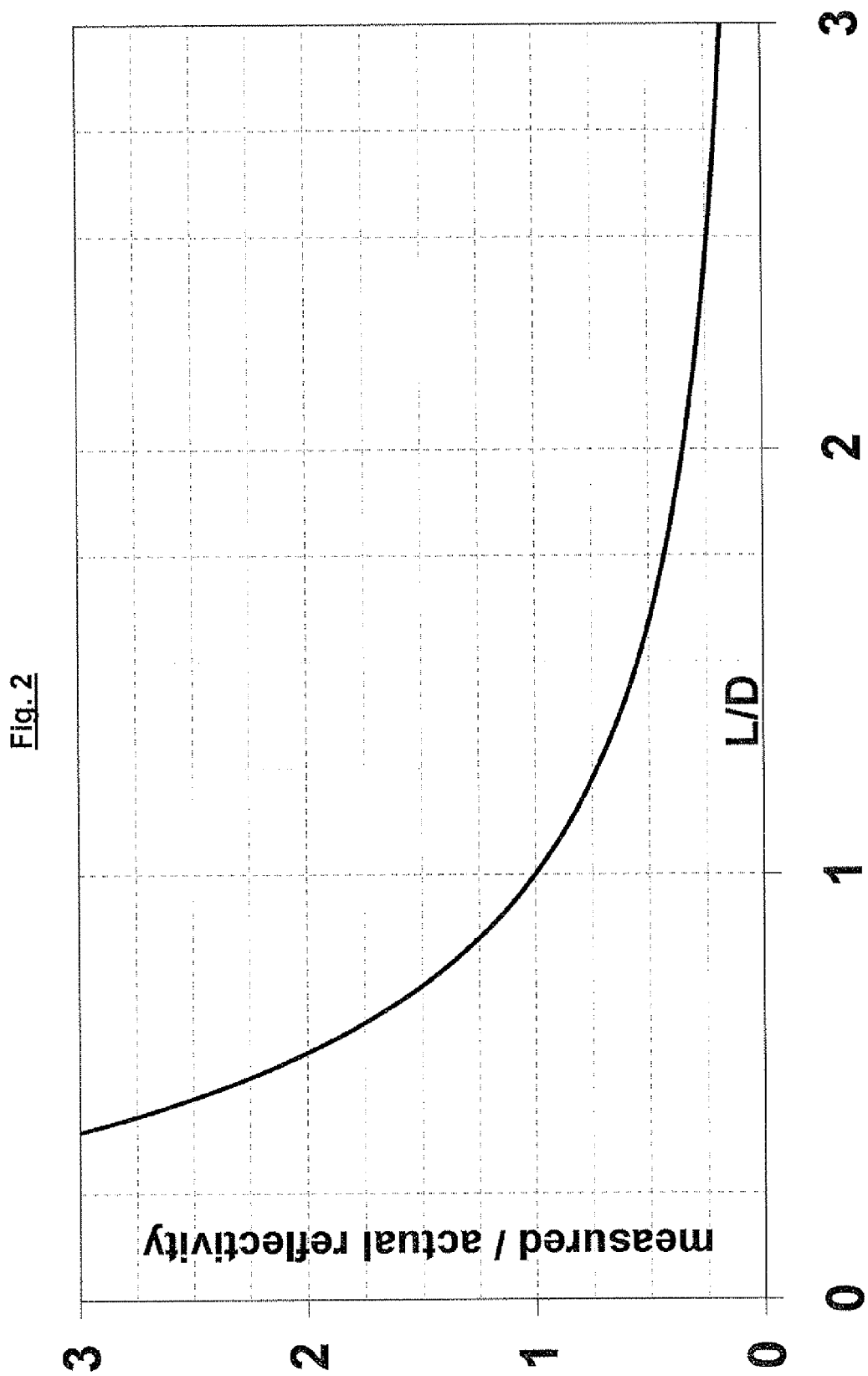
FIG. 2 shows the fractional error in measured reflectivity as a function of dimensionless probe-to-target distance (L/D), for a probe of the type shown in FIG. 1B, with a beam divergence of $\theta=30°$ and which was calibrated at L/D=1.
Figure 3:
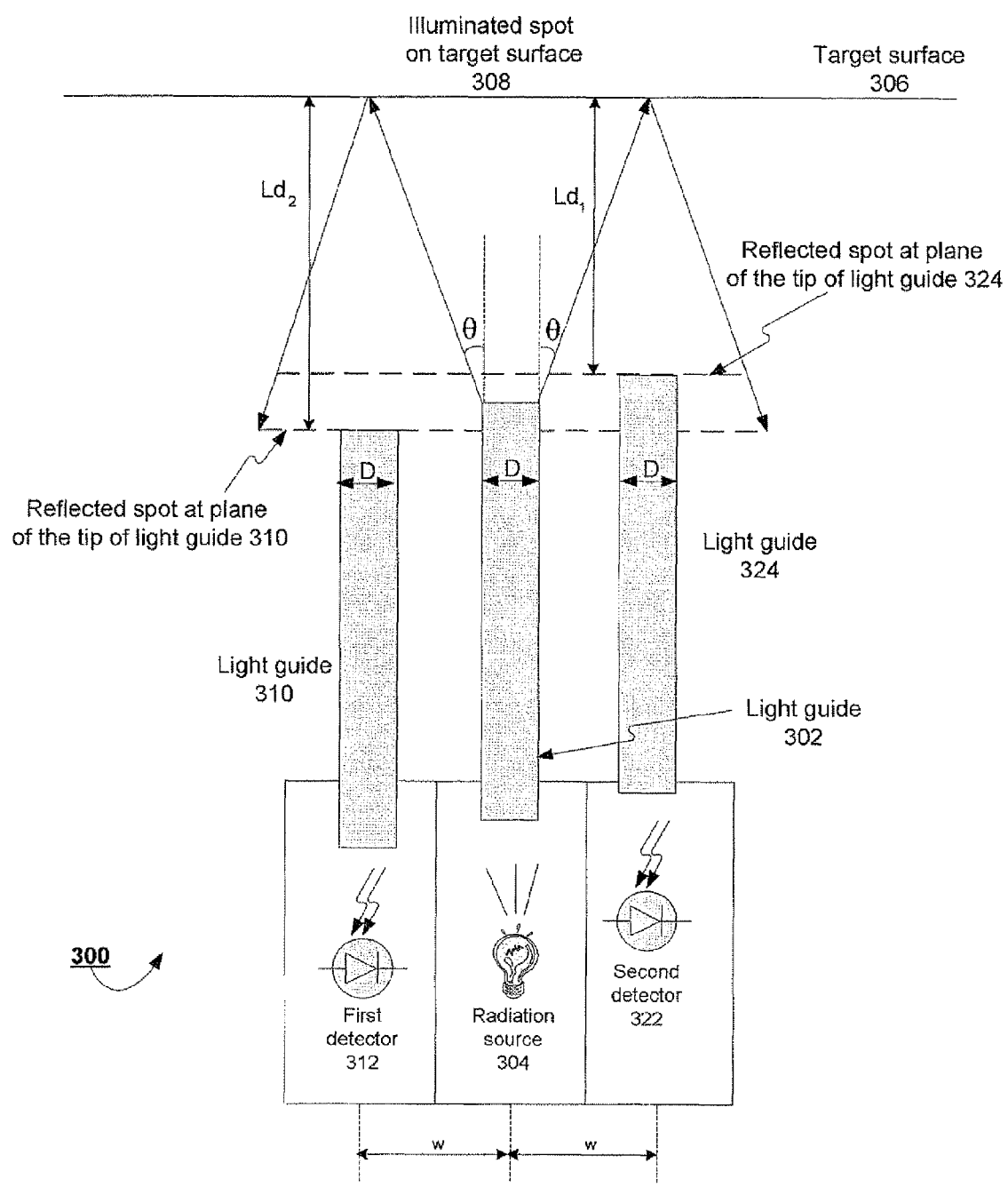
FIG. 3 shows a schematic drawing of one embodiment of a reflectivity meter of the present invention.

In the following description of the invention, the term probe tip will be used to refer to a surface of the apparatus through which radiation leaves the apparatus to impinge on the target surface, and/or a surface of the apparatus through which radiation reflected from the target surface enters the apparatus to be directed towards the detector. The term probe-to-target distance will refer to the average of the distances between the target surface and each probe tip of the apparatus In order to describe and clarify the operating principle of the invention, we begin by considering a particular implementation. After considering this particular implementation, more general embodiments will be described. FIG. 3 schematically shows a particular (first) embodiment of an apparatus 300 of the current invention. In common with apparatus 100, apparatus 300 includes a light guide 302 that directs radiation from a radiation source 304 onto a target surface 306 to form an illuminated spot 308, a second light-guide 310 and a detector 312. In addition to these elements, apparatus 300 includes a second detector 322 and a third light guide 324. Light guide 324 is of the same diameter as light-guide 310, and the axes of both of these light-guides are parallel to and equidistant from the axis of light-guide 302. However, light-guide 324 is positioned closer to the target surface (with an probe-to-target distance $L_{d2}$) than light guide 310 (with a probe-to-target distance $L_{d1}$), i.e. $L_{d2} < L_{d1}$.

This apparatus can be viewed as equivalent to two separate apparatuses 100, since the signal generated at each detector is not affected by the presence of the other light-guide/detector combination. Thus equation (3) can be used to describe the radiant power falling on each detector separately:

$$V_1 = V_{01} + \rho \eta_1 \frac{\pi (D/2)^2}{\pi (D/2 + (L_e + L_{d1})\tan\vartheta)^2} \quad (8)$$

$$V_2 = V_{02} + \rho \eta_2 \frac{\pi (D/2)^2}{\pi (D/2 + (L_e + L_{d2})\tan\vartheta)^2} \quad (9)$$

In the above two equations, subscripts ending in 1 refer to quantities associated with light-guide 310 and detector 312, while subscripts ending in 2 refer to quantities associated with light-guide 324 and detector 322. Subtracting the offset term in (8) and (9) and taking the ratio of these two equations gives:

$$\frac{V_2 - V_{02}}{V_1 - V_{01}} = \frac{\eta_2}{\eta_1} \frac{\left(1 + 2\frac{L_e + L_{d1}}{D}\tan\vartheta\right)^2}{\left(1 + 2\frac{L_e + L_{d2}}{D}\tan\vartheta\right)^2} \quad (10)$$

Figure 4:
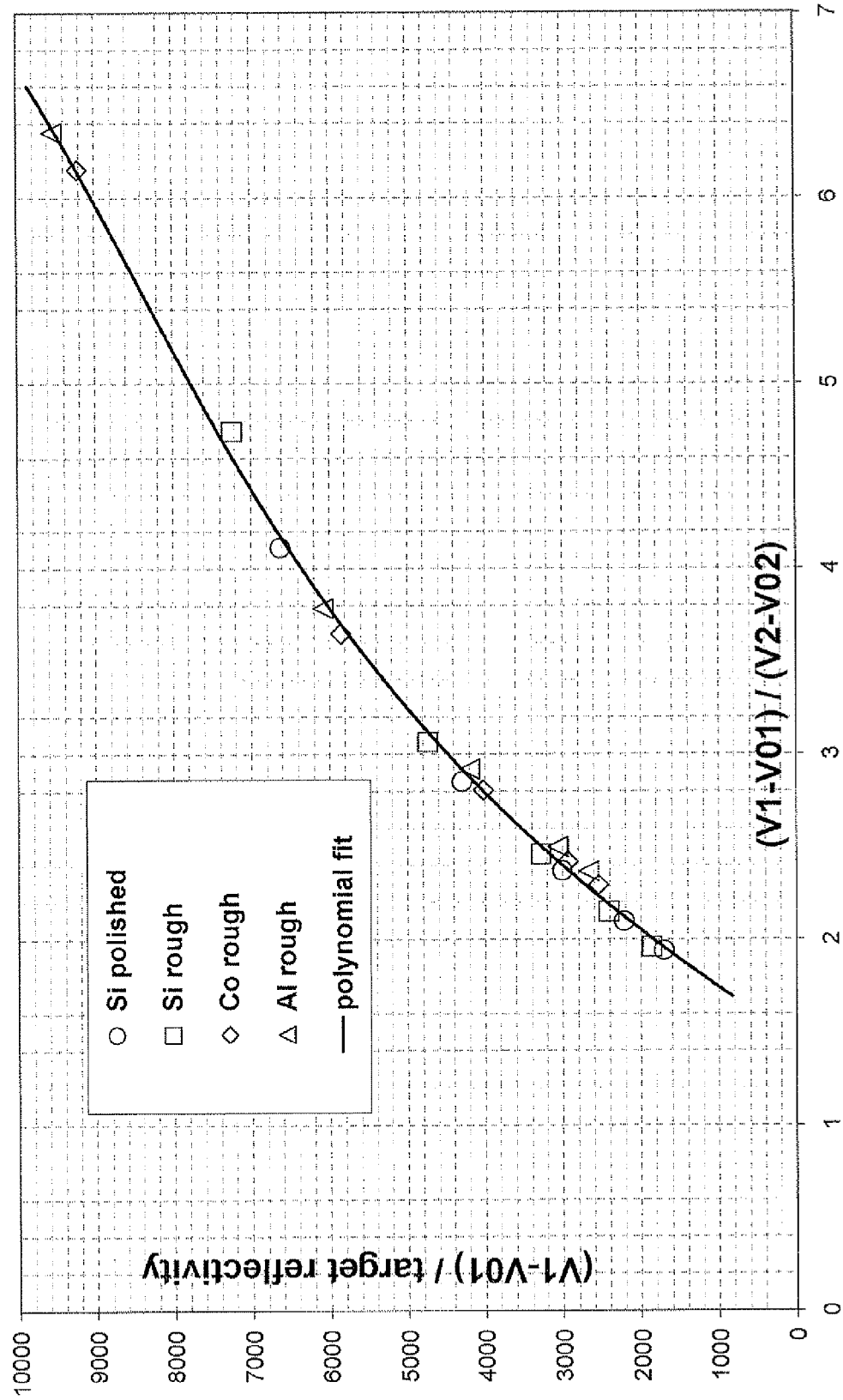
FIG. 4 shows a plot of the quantity $(V_1-V_{01})/\rho_{calibration}$ against $(V_2-V_{02})/(V_1-V_{01})$, as measured using an apparatus of the type sketched in FIG. 3, viewing various targets.

Notice that this equation shows that the ratio of signals $(V_2-V_{02})/(V_1-V_{01})$ is independent of the target reflectivity. In addition, equation (8) shows that the quantity $(V_1-V_{01})$ is proportional to the target reflectivity, and hence $(V_1-V_{01})/\rho$ is independent of the target reflectivity. It thus follows that one can plot the quantity $(V_1-V_{01})/\rho$ against the quantity $(V_2-V_{02})/(V_1-V_{01})$ for a particular apparatus at various probe-to-target distances, in order to get a curve which is independent of the target reflectivity. Stated another way, when plotting these two quantities against each other for a particular apparatus and various probe-to-target distances, the same curve will be generated regardless of the target reflectivity. FIG. 4 shows such a plot generated using an apparatus 300, viewing various targets of different reflectivities (circles=polished silicon; squares=unpolished silicon wafer; diamonds=unpolished silicon wafer coated with cobalt layer; triangles=unpolished silicon wafer coated with aluminum layer; curve=polynomial function fitted to the data). Each point in this plot corresponds to a different probe-to-target distance. The important thing to notice is that the points from all the targets fall on the same curve.

In order to use apparatus 300 to measure the reflectivity of targets of unknown reflectivity and probe-to-target distance, the following procedure may be used;

Step 1. Measure the radiant power $V_{01}$ and $V_{02}$ falling on the two detectors, while the probe is pointed at a large, open space (or any target of effectively zero reflectivity).

Step 2. Point the probe at a calibration target of known reflectivity $\rho_{calibration}$, using a number of probe-to-target distances, and record the reflected radiant power $V_1$ and $V_2$ falling on each detector for each probe-to-target distance. It is not necessary to know the probe-to-target distances at which each signal pair is measured, only to vary this distance generally about the expected distance where unknown targets will later be placed for future measurement. Note that the combined probe is moved as a unit relative to the target surface, so that each light-guide remains fixed relative to the other light-guides.

Step 3 After measuring the signals $V_1$ and $V_2$ generated by each detector at the various (unmeasured) probe-to-target distances, make a plot of the quantity $(V_1-V_{01})/\rho_{calibration}$ against the quantity $(V_2-V_{02})/(V_1-V_{01})$. A curve $f$ can be fit to this data, such that $$\frac{V_1 - V_{01}}{\rho_{calibration}} = f\left\{\frac{V_2 - V_{02}}{V_1 - V_{01}}\right\} \quad (11)$$

Note that the same function $f$ will be generated irrespective of what calibration target is used, so more generally we can write $$\frac{V_1 - V_{01}}{\rho} = f\left\{\frac{V_2 - V_{02}}{V_1 - V_{01}}\right\} \quad (12)$$

Step 4. Now direct the probe at a target of unknown reflectivity, to measure a new pair of signals $V_1$ and $V_2$ at detectors 312 and 322 respectively. Plugging these signals into equation (12) and solving for the unknown target reflectivity $\rho$ gives:

$$\rho = \frac{V_1 - V_{01}}{f\left\{\frac{V_2 - V_{02}}{V_1 - V_{01}}\right\}} \quad (13)$$

Note that while the above four step calibration and measurement procedure was described within the context of a particular probe geometry and model, this was done only for the purpose of clarity while explaining the method. We now describe the more general design requirements and operation procedures of the invention.

Figure 5:
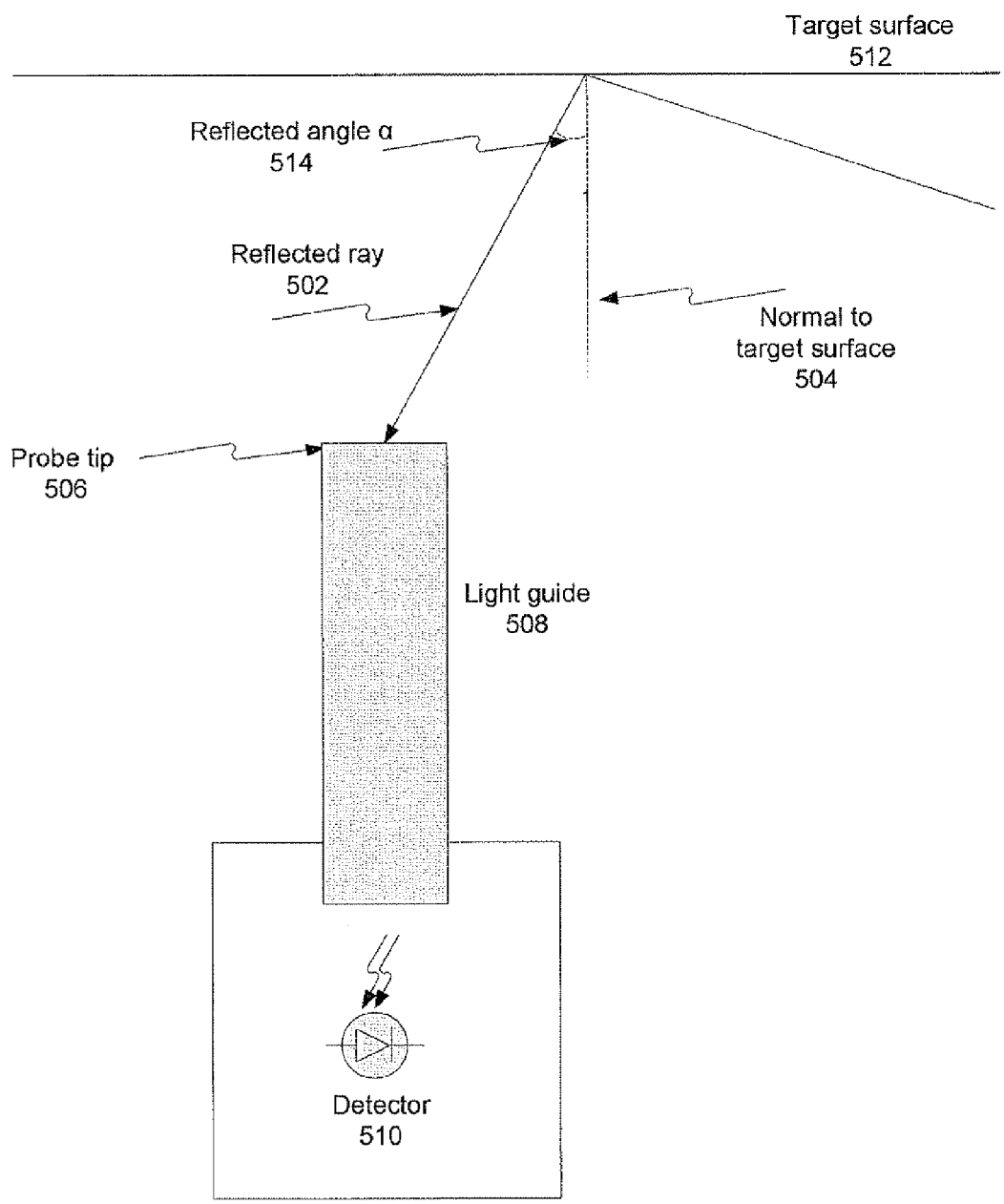
FIG. 5 shows the definition of a "reflected angle" α, measured relative to the target surface normal vector.

The general statement of the requirements of the apparatus hardware is that it must be capable of measuring at least two reflected radiant intensities from the target surface, with each measurement sampling the reflected radiation in a different distribution of reflected angles. The exact meaning of "reflected angle" is defined in FIG. 5, which shows a "ray" 502 of reflected radiation leaving the target surface at a "reflected angle" $\alpha$ with respect to the target surface normal 504, and entering a probe tip 506.

Figure 6:
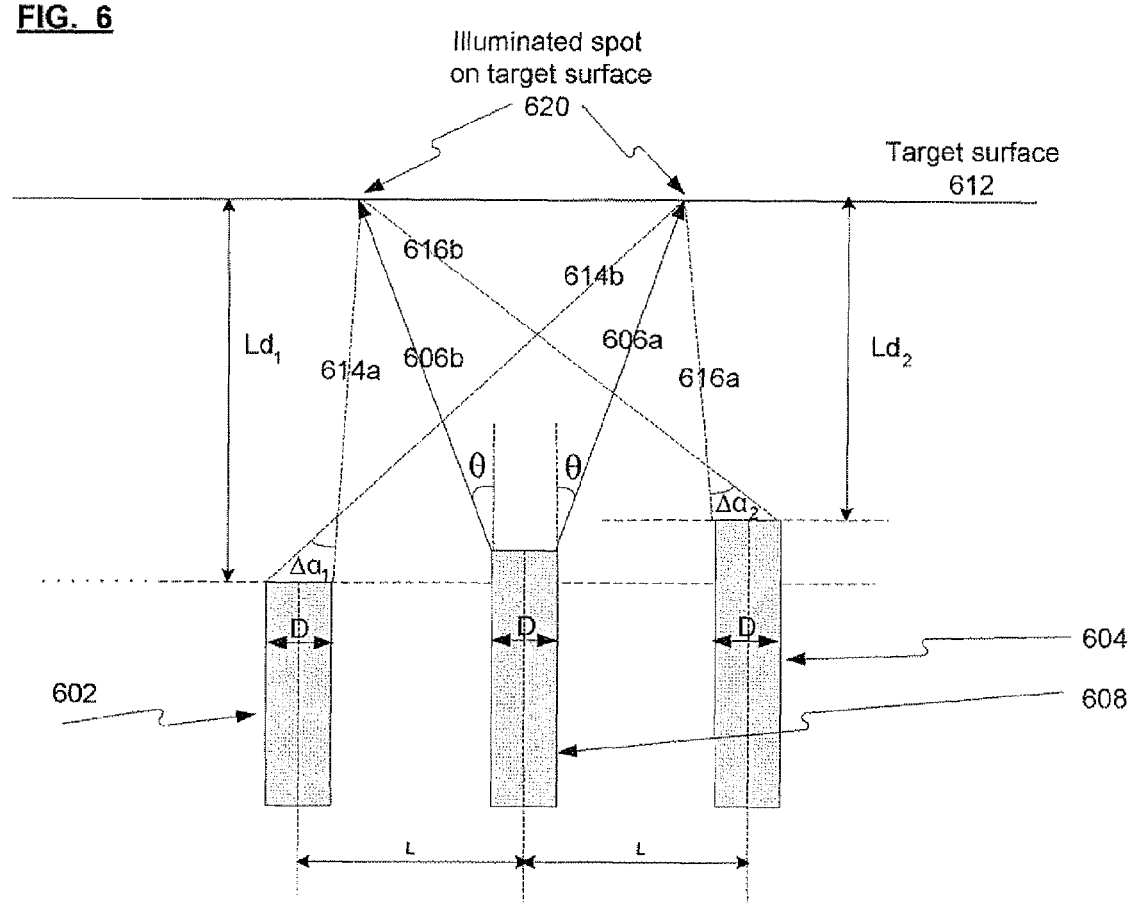
FIG. 6 demonstrates the apparatus of FIG. 3 collecting reflected radiation at two different angular distributions.

FIG. 6 demonstrates that embodiment 300 of the invention is in fact an implementation of the invention as described in the previous paragraph, since each of two collecting light-guides 602 and 604 collects radiation in a different range of reflected angles. In this figure, solid lines 606a and 606b exiting a central light guide 608 at an angle $\theta$ indicate the maximum extent of an illuminating beam incident on a target surface 612. Dotted lines 614a,b and 616a,b leading from the edges of the illuminated spot on target surface 612 to the edges of collecting light-guides 602 and 604 respectively indicate the minimum and maximum reflected angles collected by each of these probes. The difference between the minimum and maximum reflected angle collected by light guide (probe) 602 is marked $\Delta\alpha_1$, and this difference for probe 604 is marked $\Delta\alpha_2$. Simple geometric arguments can be used to show that $L_{d1} > L_{d2}$ implies $\Delta\alpha_1 < \Delta\alpha_2$. Hence different reflected angular distributions are collected by each probe.

The requirement in the present invention that each of the two or more measurements collect radiation at a different distribution of reflected angles stems from the need to ensure that the ratio of these reflected intensity measurements (after subtracting any offset signal) be a function of the probe-to-target distance. If all the reflected intensity measurements collected radiation at identical reflected angular distributions, then the ratio of the measurements would be a constant, independent of probe-to-target distance, and it would be impossible to fit a function $f$ to equation (12).

In general, any reflected intensity measurement will be proportional to the target reflectivity (after subtracting offset signals). From this it follows that the ratio of two reflected intensities is independent of the target reflectivity. Thus a plot of the type shown in FIG. 4 can be generated for any system that satisfies the requirement that each measurement is taken at a different angle distribution, and such plots will be independent of the reflectivity of the target. From this it further follows that the four step calibration and measurement procedure described above with reference to apparatus 300, can in fact be used with any apparatus that satisfies the requirement of collecting radiation in at least two different reflected angular distributions. Thus the four step procedure is in fact a general calibration and operation procedure for the invention.

As stated in the previous paragraph, the operation of the invention relies on the ratio of the two reflected intensities being independent of the target reflectivity. However, since the reflectivity of a target surface is generally a function of the viewing angle, it is possible that the target reflectivity will be somewhat different for each reflected angle distribution. In such a case, the target reflectivity will not exactly cancel when taking the ratio of the two reflected intensities. We note that rough surfaces are generally Lambertian (reflectivity is not a function of viewing angle) and hence the difference in sampling angle between the measurements is not a problem for such surfaces. For polished surfaces, however, there could potentially be a measurement error if the two measurements sample reflected radiation at angular distributions which vary too widely. For this reason, it is desirable that the angular distributions sampled by each reflected intensity measurement be similar enough that the target reflectivity be nearly the same across all the distributions. However, it is also necessary that the reflected angle distributions be different enough that the ratio of reflected intensities be a detectable function of probe-to-target distance (i.e. detectable above the measurement noise). Practically speaking, it is possible to reconcile these two requirements into an apparatus design which can accurately measure a wide variety of both polished and rough surfaces, as is indicated by the fact that the data of FIG. 4 fall on a single curve while viewing a number of different surfaces using an apparatus 300.

Figure 7:
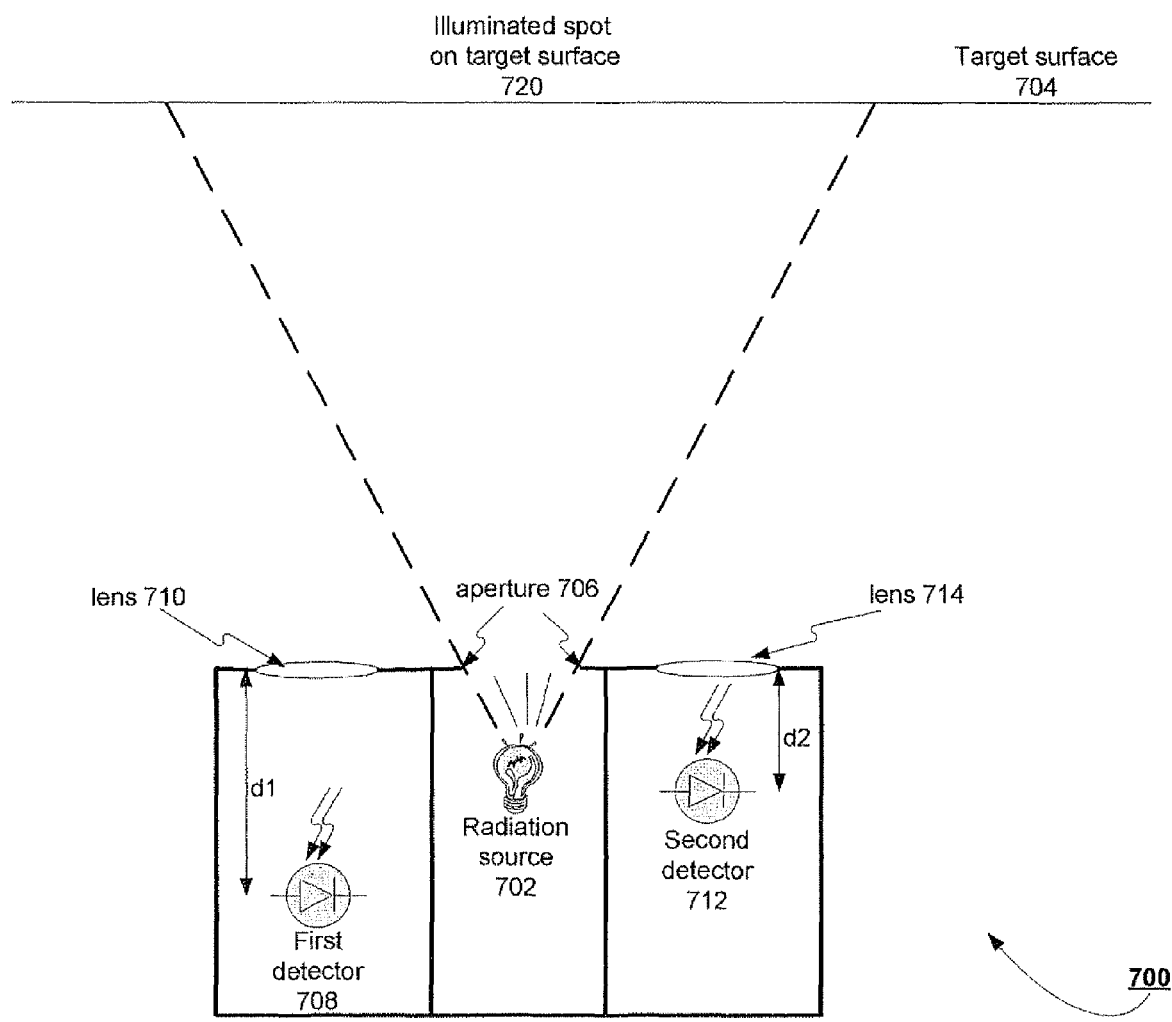
FIG. 7 shows a schematic drawing of another reflectivity meter of the present invention, using two detector/lens pairs focused at different positions.
Figure 8:
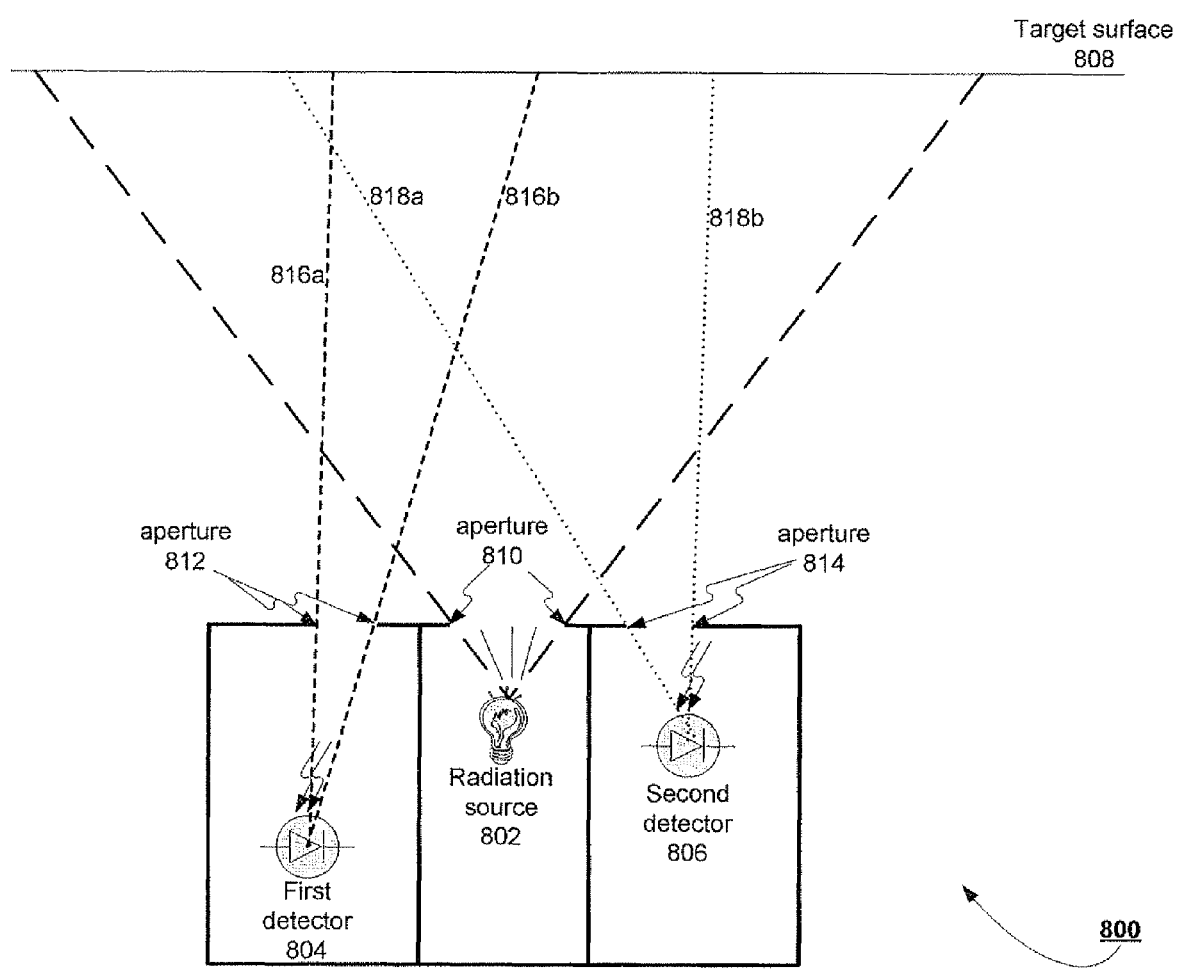
FIG. 8 shows a schematic drawing of another reflectivity meter of the present invention, using two apertures of different sizes and positions, to collect reflected radiation for detection.

In addition to apparatus 300, numerous other designs can produce measurements of reflected intensity at varying angular distributions. For example, the light-guides of apparatus 300 can be replaced with lenses focused at different distances from the target surface. Such an implementation of the invention is shown in FIG. 7, which depicts radiation source 702 illuminating the target surface 704 via aperture 706. The reflected radiation is sampled by two lens+detector pairs, which are identical with the single exception that the first detector 708 is positioned at a distance d1 from lens 710, while the second detector 712 is placed at a distance d2 from lens 714, with d2<d1. For such a system, lens and detector pair 708, 710 will collect radiation from a narrower angle range than lens-detector pair 714, 712. Another embodiment of the apparatus (not shown) may use radiation sources of differing illumination angle, which would produce differing spot sizes on the target surface. This, in turn, would produce different angle ranges collected by the collecting probes (as can be seen by looking at FIG. 6 and considering what happens to the angle range $\Delta\alpha$ when the illuminated spot size changes). Similarly, FIG. 8 shows an implementation of the invention using a single radiation source 802 and two detectors 804 and 806, all of which shine/collect radiation to/from the target surface 808 via exit/entrance probes 810, 812, and

814 respectively. The size and position of apertures 812 and 814 with respect to detectors 804 and 806, respectively, are such that each of detectors 804 and 806 collect radiation at a different angular distribution. The acceptance angles for each detector are illustrated by dotted lines 816a and 816b for detector 804, and dotted lines 818a and 818b for detector 806. Yet other implementations of the invention are obtained if each radiation source in FIGS. 3, 7, and 8 is replaced by a detector, while each detector in these figures is replaced by a radiation source.

Note that while FIG. 4 shows plots of $(V_1-V_{01})/\rho_{calibration}$ against $(V_2-V_{02})/(V_1-V_{01})$, it is also possible to implement the invention using plots of other functions of the measured signals. For example, any function of the signal ratio $(V_2-V_{02})/(V_1-V_{01})$ can be plotted against any function of the signal $(V_1-V_{01})/\rho_{calibration}$, to produce a curve that is independent of the target reflectivity. Plotting a function of these quantities, rather than the quantities themselves, may potentially simplify the form of the fitting function $f$, and/or improve signal-to-noise in the function fit.

While the invention was described mainly within the context of the measurement of two reflected intensities, each with a different angular distribution, it is also possible to implement the invention using a larger number of measured reflected intensities (with at least two different angular distributions among the multiple measurements). In this case, some method to combine these many measured intensities is needed in order to calculate a single reflectivity value. For example, one could calculate multiple reflectivity values using various pairs of the multiple measured intensities, and average over these calculated values to get a single measurement result. The advantage of such an approach is that the averaging may decrease the measurement noise, and the spread of the multiple calculated reflectivity values can give an indication of the uncertainty in the averaged reflectivity value.

The invention was described above with regard to radiant power or intensity falling on the apparatus detector. However, the invention may also be realized using detectors that measure other quantities, such as a number of photons (using a quantum detector), in which case the calculated reflectivity will indicate the fraction of reflected photons, rather than the fraction of reflected power.

In the various figures, the illuminating and detecting sections of the apparatus were shown using separate light-guides, lenses, apertures, etc. This was done primarily in order to improve the clarity of the description. In practice, in some embodiments, it may be desirable to use beam-splitters, bifurcated fiber bundles, etc. to combine the emitting and collecting functions of the apparatus probe(s) into a single optical path, using standard optical design techniques. This could be convenient in implementation of the invention, as it allows for a simpler and more compact probe head.

The apparatuses shown in FIGS. 3, 7 and 8 were discussed within the context of a simultaneous measurement of at least two reflected radiant intensities, each at a different angular distribution. However, these at least two intensities could also be measured sequentially. Such a sequential measurement would in particular be useful for implementations involving two radiation-sources and only one detector, where the reflected intensity from each radiation source would be measured while the other radiation source was "off" (i.e. not radiating onto the target surface). Alternatively, each radiation source could be modulated at a different frequency or phase, and the signal from the single detector could be separated into components corresponding to the modulation frequency or phase from each radiation source respectively, using standard signal processing techniques. Another example of an implementation of the invention using sequential measurement of the two or more reflectivities is illustrated in FIG. 9. This apparatus is comprised of a radiation-source 902 and a detector 904, as well as a method of reproducibly moving the probe between two positions, one closer to the target surface than the other. In FIG. 9, the position closer to the target surface is indicated by dotted lines 906, while the position farther from the target surface is indicated by solid lines 908. The apparatus should measure a first signal when it is at the position near the target surface, and a second signal when the apparatus is farther from the target surface. The signal collected when the probe is farther from the target surface will have a smaller reflected angle distribution than the signal collected closer to the target surface.

A variation of this invention can allow the apparatus to measure the distance L between the target surface and the probe. This is possible if during the calibration procedure, the distance L is carefully measured for each measured value of the signal ratio $(V_2-V_{02})/(V_1-V_{01})$. Then it is possible to fit a function g to the data pairs $\{L, (V_2-V_{02})/(V_1-V_{01})\}$. When viewing subsequent targets at unknown distance from the probe, the probe-to-target distance can be calculated from the measured intensities using the relation:

$$L = g\left\{\frac{V_2 - V_{02}}{V_1 - V_{01}}\right\} \tag{10}$$

One major application of known reflectivity meters is in temperature measurement. In this application, the target reflectivity is measured as described in the Background section above, and this measurement is used to infer the target emissivity. In particular, when the reflectivity measurement is made at a wavelength range where the target is opaque, the emissivity of the target surface $\epsilon$ is related to the target reflectivity $\rho$ through the simple relation $\epsilon=1-\rho$. This emissivity value is combined with a measurement of the target self-emission, to infer the target temperature. Such thermometers are used for example for non-contact temperature measurement of semiconductor substrates during microelectronics device fabrication, and specific models used for this purpose are listed in the Background section above.

Frequently in microelectronics processing, the exact position of the substrate whose temperature is to be measured is not precisely fixed, since the various processing steps in microelectronics fabrication can cause the substrate to warp from its nominal position, due to e.g. thermal effects or the effects of added/removed layers from the substrate. Additionally, the movement/rotation of the substrate during processing also introduces some uncertainty in its exact position. Thus in many processing steps, prior art reflectivity meters give inaccurate reflectivity measurements, which result in inaccurate temperature measurements. The present invention provides an improved reflectivity measurement apparatus and method as described above. Therefore, temperature probes incorporating a reflectivity meter that is insensitive to the exact position of the substrate relative to the measurement probe, as provided by the present invention, represent a significant breakthrough, and allow accurate temperature measurement for those processes where the position of the substrate is not precisely fixed.

All publications and patents mentioned in this specification are incorporated herein in their entirety by reference into the specification, to the same extent as if each individual publication or patent was specifically and individually indicated to be incorporated herein by reference. In addition, citation or identification of any reference in this application shall not be construed as an admission that such reference is available as prior art to the present invention.

What is claimed is:

1. An apparatus for determining the reflectance of a target surface comprising:
   a. a radiation source for projecting radiation onto the target surface;
   b. a radiation detector positioned to detect radiation reflected off the target surface at least two different locations of said radiation detector relative to said radiation source and to the target surface and to produce at least two respective signals V1 and V2 such that each signal is indicative of a radiation intensity reflected at a respective angular distribution that is different for each signal, wherein at least two of said angular distributions overlap at least partially;
   whereby signals V1 and V2 are used to calculate the reflectivity of the target surface.

2. The apparatus of claim 1, further comprising:
   c. a light guide having an entrance aperture with a diameter D, the light guide interposed in an optical path between the target surface and the radiation detector, wherein the different angular distribution is obtained by respective measurements at different aperture-to-target surface distances.

3. The apparatus of claim 2, wherein the measurements are performed sequentially.

4. The apparatus of claim 2, further comprising:
   d. an additional radiation detector positioned to detect radiation reflected off the target surface; and
   e. an additional light guide having an entrance aperture with diameter D2, the additional light guide interposed in an optical path between the target surface and the additional radiation detector, wherein the measurements are performed simultaneously.

5. The apparatus of claim 1, further comprising:
   c. at least one additional radiation detector positioned to detect radiation reflected off the target surface;
   d. a lens interposed in an optical path between each radiation detector and the target surface, each lens and detector on a given optical path forming a lens-detector pair, wherein each lens is focused to a different distance, such that each lens-detector pair collects reflected radiation at a different angular distribution.

6. The apparatus of claim 1, further comprising:
   c. an additional radiation source, wherein the two radiation sources form different size spots on the target surface, thereby causing the angular distribution to be different for each signal.

7. The apparatus of claim 1, wherein the calculation is performed using the formula $\rho=(V1-V01)/f\{(V2-V02)/(V1-V01)\}$, where $\rho$ is the calculated reflectivity of the measured target surface, V01 and V02 are readings of the apparatus when viewing a target of nearly zero reflectivity, and $f$ is a calibration function generated using a target of known reflectivity $\rho$calibration.

8. An apparatus for determining the reflectance of a target surface comprising:
   a. a radiation source for projecting radiation onto the target surface;
   b. a radiation detector positioned to detect radiation reflected off the target surface at least two different locations of said radiation detector relative to said radiation source and relative to the target surface and to produce at least two respective signals V1 and V2 such that each signal is indicative of a radiation intensity reflected at a respective angular distribution that is different for each signal, wherein at least two said angular distributions overlap at least partially, and wherein signals V1 and V2 differ from each other in that each respective angular distribution is determined by a respective different aperture.

9. The apparatus of claim 8, wherein the respective aperture is placed along an optical path between the radiation source and the target surface, at distance to the target surface different for each aperture.

10. The apparatus of claim 8, wherein the respective aperture is placed along an optical path between the radiation detector and the target surface, at distance to the target surface different for each aperture.

11. The apparatus of claim 8, wherein each aperture has a different diameter.

12. The apparatus of claim 8, operated as a probe tip to target distance meter.

13. A method for determining the reflectance of a target surface comprising the step of:
   a. detecting radiation reflected from the target surface, at least two different locations of a radiation detector relative to a source of said radiation and relative to the target surface, in at least two different respective angular distributions, wherein each angular distribution produces a respective different reflected radiation intensity value and wherein two of said at least two different angular distributions overlap at least partially; and
   b. calculating the target reflectivity from the at least two different reflected radiation intensity values.

14. The method of claim 13, wherein the step of detecting is performed sequentially by a single radiation detector.

15. The method of claim 13, wherein the step of detecting is performed simultaneously by using a dedicated radiation detector for each angular distribution.

16. The method of claim 13, wherein the different angular distributions are induced by illuminating the target surface with different illumination spot sizes.

17. The method of claim 13, wherein the different angular distributions are induced by passing the reflected radiation through different size apertures positioned between the target surface and respective different radiation detectors.

18. The method of claim 13, wherein the different angular distributions are induced by illuminating the surface with radiation originating from at least two apertures positioned at different distances from the target surface.

19. The method of claim 13, wherein the different angular distributions are induced by illuminating the surface with radiation originating from at least two apertures having different diameters.

20. The method of claim 13, wherein the step of calculating includes:
   i. detecting radiation reflected from a target surface of near zero reflectivity in at least two different angular distributions and producing at least two respective signals V01 and V02 indicative of the radiation intensity at respective angular distributions 1 and 2;
   ii. generating a calibration function $f$ by performing the step of detecting on a target of known reflectivity $\rho$calibration, and
   ii. using signals V01 and V02 and calibration function $f$ to calculate the target reflectivity.

21. The method of claim 20, wherein the target reflectivity calculation is done according to the formula $\rho=(V1-V01)/f\{(V2-V02)/(V1-V01))$, where V1 and V2 are signals indicative of a radiation intensity reflected at a respective angular distribution that is different for each signal.

22. The method of claim 13, wherein the different angular distributions are achieved through reflected radiation emanating from multiple radiation sources, wherein each radiation source intensity is modulated with a different frequency and/or phase.

23. An apparatus for determining the reflectance of a target surface comprising:
   a. a radiation source for projecting radiation onto the target surface;
   b. a radiation detector positioned to detect radiation reflected off the target surface at least two different locations of said radiation detector relative to said radiation source and relative to the target surface and to produce at least two signals V1 and V2 such that each signal is indicative of a radiation intensity reflected at a respective angular distribution that is different for each signal; wherein signals V1 and V2 are used to calculate the reflectivity of the target surface without explicit use of a reference reflectivity.

24. An apparatus for determining the reflectance of a target surface comprising:
   a. a radiation source for projecting radiation onto the target surface;
   b. a radiation detector positioned to detect radiation reflected off the target surface at least two different locations of said radiation detector relative to said radiation source and relative to the target surface and to produce at least two signals V1 and V2 such that each signal is indicative of a radiation intensity reflected at a respective angular distribution that is different for each signal, wherein signals V1 and V2 differ from each other in that each respective angular distribution is determined by a respective different aperture, and wherein signals V1 and V2 are used to calculate the reflectivity of the target surface without explicit use of a reference reflectivity.

25. A method for determining the reflectance of a target surface comprising the step of:
   a. projecting radiation onto the target surface;
   b. detecting radiation reflected from the target surface, at least two different locations of a radiation detector relative to a source of said radiation and relative to the target surface, in at least two different respective angular distributions, each angular distribution producing a respective different reflected radiation intensity value; and
   b. calculating the target reflectivity from the at least two different reflected radiation intensity values without explicit use of a reference reflectivity.

* * * * *

UNITED STATES PATENT AND TRADEMARK OFFICE
CERTIFICATE OF CORRECTION

PATENT NO. : 7,742,171 B2 Page 1 of 1
APPLICATION NO. : 11/834030
DATED : June 22, 2010
INVENTOR(S) : Yoram Naor and Benjamin J Brosilow It is certified that error appears in the above-identified patent and that said Letters Patent is hereby corrected as shown below:

Claim 13 , column 12 should be corrected as follows:

Line 23: insert the word --at-- before the word "least"

Claim 24, column 14 should be corrected as follows:

Line 2: insert the word --at-- before the word "least"

Claim 25, column 14 should be corrected as follows:

Line 17: insert the word --at-- before the word "least"

Signed and Sealed this

Twenty-first Day of December, 2010

David J. Kappos
*Director of the United States Patent and Trademark Office*